United States Patent
Bruna

(10) Patent No.: US 8,739,790 B2
(45) Date of Patent: *Jun. 3, 2014

(54) ELECTRONIC DISPLAY DEVICE AND A FLUID DISPENSER DEVICE INCLUDING SUCH A DISPLAY DEVICE

(75) Inventor: Pascal Bruna, Sotteville les Rouen (FR)

(73) Assignee: Aptar France SAS, Le Neubourg (FR)

( * ) Notice: Subject to any disclaimer, the term of this patent is extended or adjusted under 35 U.S.C. 154(b) by 1377 days.

This patent is subject to a terminal disclaimer.

(21) Appl. No.: 10/532,073

(22) PCT Filed: Oct. 24, 2003

(86) PCT No.: PCT/FR03/03159
§ 371 (c)(1),
(2), (4) Date: Apr. 21, 2005

(87) PCT Pub. No.: WO2004/040536
PCT Pub. Date: May 13, 2004

(65) Prior Publication Data
US 2006/0011651 A1    Jan. 19, 2006

(30) Foreign Application Priority Data
Oct. 28, 2002 (FR) ................................ 02 13470

(51) Int. Cl.
*A62B 7/00* (2006.01)

(52) U.S. Cl.
USPC ............ 128/205.23; 128/200.14; 128/200.23; 222/36

(58) Field of Classification Search
USPC ............ 222/36, 30, 32, 38, 23, 162, 50, 504; 128/203.23, 205.23, 200.14, 200.22, 128/200.23, 200.24, 200.12, 203.15; 377/6, 377/13, 15–16
See application file for complete search history.

(56) References Cited

U.S. PATENT DOCUMENTS

| | | | | |
|---|---|---|---|---|
| 4,051,998 A | * | 10/1977 | Zabel | 705/413 |
| 4,131,215 A | * | 12/1978 | Hansel | 222/26 |
| 5,544,647 A | * | 8/1996 | Jewett et al. | 128/200.23 |
| 5,564,414 A | * | 10/1996 | Walker et al. | 128/200.23 |
| 5,755,218 A | * | 5/1998 | Johansson et al. | 128/200.14 |
| 5,895,159 A | * | 4/1999 | Liou | 401/2 |
| 6,029,659 A | * | 2/2000 | O'Connor | 128/203.12 |
| 6,188,742 B1 | | 2/2001 | Schousek et al. | |
| 6,327,017 B2 | * | 12/2001 | Barberi et al. | 349/177 |
| 2002/0195988 A1 | | 12/2002 | LeDoux et al. | |
| 2004/0097873 A1 | * | 5/2004 | Langley et al. | 604/67 |
| 2006/0289008 A1 | * | 12/2006 | Rand et al. | 128/203.15 |

FOREIGN PATENT DOCUMENTS

| | | |
|---|---|---|
| EP | 1 098 235 A | 5/2001 |
| GB | 1036464 | 7/1966 |
| GB | 2 191 326 A | 12/1987 |
| JP | 58019169 | 2/1983 |
| JP | 06038543 | 2/1994 |
| JP | 06245588 | 9/1994 |

* cited by examiner

Primary Examiner — Frederick C Nicolas
(74) Attorney, Agent, or Firm — Sughrue Mion, PLLC

(57) ABSTRACT

An electronic display device (20) including a display member (21). The display member (21) is permanent so that no energy is required to keep the display unchanged. The display device (20) operates without a battery, the energy required to change the display being created by interaction between two elements, such as by friction or by an impact, thereby creating an electric pulse that is processed by an electronic circuit (25) before being applied to the display member (21) in order to change its display.

15 Claims, 1 Drawing Sheet

ELECTRONIC DISPLAY DEVICE AND A FLUID DISPENSER DEVICE INCLUDING SUCH A DISPLAY DEVICE

FIELD OF THE INVENTION

The present invention relates to an electronic display device and to a fluid dispenser device including such a display device.

BACKGROUND

Electronic display devices are widely used in a large number of technical fields. A particular field of use is constituted by dose indicators used with fluid dispenser devices, in particular in the pharmaceutical field. In particular, such dose indicators make it possible to inform the user of the number of doses that have been dispensed or that remain to be dispensed. In such a use, an electric signal is generally generated while the dose is being dispensed, i.e. while the dispenser is being actuated, the electric signal then being processed electronically and transferred to an electronic display in order to change the display, i.e. to count one dose up or down. The displays are generally constituted by liquid crystal displays (LCDs). In order to operate, such indicators, and more generally electronic display devices, need to use a source of electricity, which is generally an optionally-rechargeable battery, or possibly a mains connection. That type of energy source is relatively costly to provide and to install, thereby correspondingly increasing the cost of manufacturing and of using the medication dispenser. In particular, equally costly control electronics are required to control and manage the energy source.

Objects of Preferred Embodiments of Invention

An object of the present invention is to provide an electronic display device which does not have the above-mentioned drawbacks.

Another object of the present invention is to provide a fluid dispenser including a dose indicator which does not have the above-mentioned drawbacks.

More particularly, an object of the present invention is to provide an electronic display device which is simple and inexpensive to manufacture and to assemble.

Another object of the present invention is to provide such an electronic display device that is compact and that can be easily adapted to any kind of existing fluid dispenser device without having to modify its dimensions substantially.

Another object of the present invention is to provide such a display device that operates in reliable manner regardless of the length of time the device has been used or in storage, and while not requiring a power supply in order to cause said device to operate.

The present invention therefore provides an electronic display device including a display member, said display member being permanent so that no energy is required to keep the display unchanged, said display device operating without a battery, the energy required to change the display being created by interaction between two elements, such as by friction or by an impact, thereby creating an electric pulse, said pulse being processed by an electronic circuit before being applied to the display member in order to change its display.

Advantageously, said display member is of the liquid crystal display (LCD) type.

Advantageously, said display member includes bistable nematic crystals.

Advantageously, said display device forms part of a dose indicator or counter for a fluid dispenser device.

The present invention also provides a fluid dispenser device comprising: a body; a fluid reservoir; a dispenser member, such as a pump or a valve; and a dose indicator for counting the number of doses that have been dispensed or that remain to be dispensed from the reservoir, said dose counter including a display device as described above.

The interaction between two portions of said device moving relative to each other while the device is being actuated, is advantageously transformed by an electro-mechanical converter into an electric pulse used to change the display.

The electric pulse required to change the display is advantageously created by a striker pin that is displaced against a contactor while the dispenser device is being actuated.

Advantageously, said contactor is held stationary relative to the body, and said striker pin co-operates with a spring.

BRIEF DESCRIPTION OF THE DRAWINGS

Other characteristics and advantages of the present invention appear more clearly from the following detailed description of a particular embodiment of the present invention, given by way of non-limiting example, and with reference to the accompanying drawing, and in which.

DETAIL DESCRIPTION OF PREFERRED EMBODIMENTS OF THE INVENTION

One of the main purposes of the present invention is to provide a display member which consumes as little energy as possible, and which does not require a power supply, so that there is no risk of said supply running out, as can occur with batteries, whether rechargeable or otherwise, in particular when the storage or usage times are very long. In addition, no electronics is needed for controlling or managing the energy source.

The electronic display device of the present invention therefore uses a display member 21 of the permanent type, i.e. of the type in which no energy is required to keep the display unchanged, and only a very small amount of energy is required to change the display. This type of display member can be of the LCD type, and more particularly, the display member 21 preferably includes bistable nematic crystals.

In order to create the energy required to change the display of the display member 21, the present invention envisages using the interaction between two elements which move relative to each other. By way of example, such interaction can be constituted by the two elements rubbing or being struck against each other. An electro-mechanical converter is preferably used to transform said interaction into an electric pulse. Suitable electro-mechanical converters can include a piezoelectric generator or actuator, an electromagnetic coil, or any other electromechanical-conversion device known to the person skilled in the art. More particularly, a flint-type system, or a piezoelectric ceramic of the type used in gas-lighters, can be used in the present invention.

Thus, the interaction between the two moving elements enables an electric pulse to be created, said electric pulse typically having a duration lying in the range 1 millisecond (ms) to 50 ms, and reaching 10000 volts (V) to 50000 V. An electronic circuit 25 is provided to process the electric pulse and to power the display member 21 so as to cause its display to change.

Figure 2:
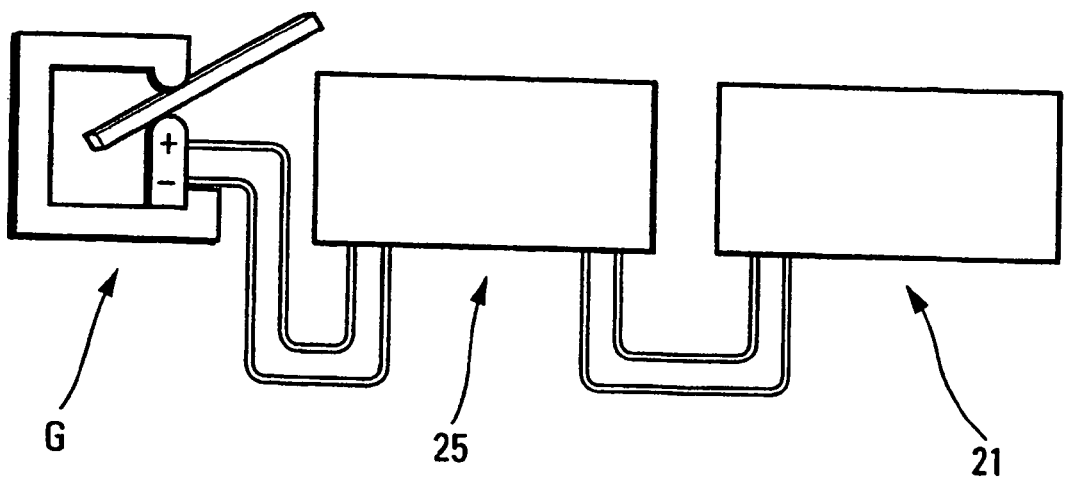
FIG. 2 is a block diagram of the display device constituting an embodiment of the present invention.

FIG. 2 is a diagram showing the operation of the display device. The generator G (electromechanical converter) creates an electric pulse which is processed by the electronic circuit 25 before being delivered to the display member 21. The generator operates without a battery, more generally without any permanent external power supply, the energy required to create the electric pulse coming from conversion of a force or a mechanical displacement into an electric signal.

Figure 1:
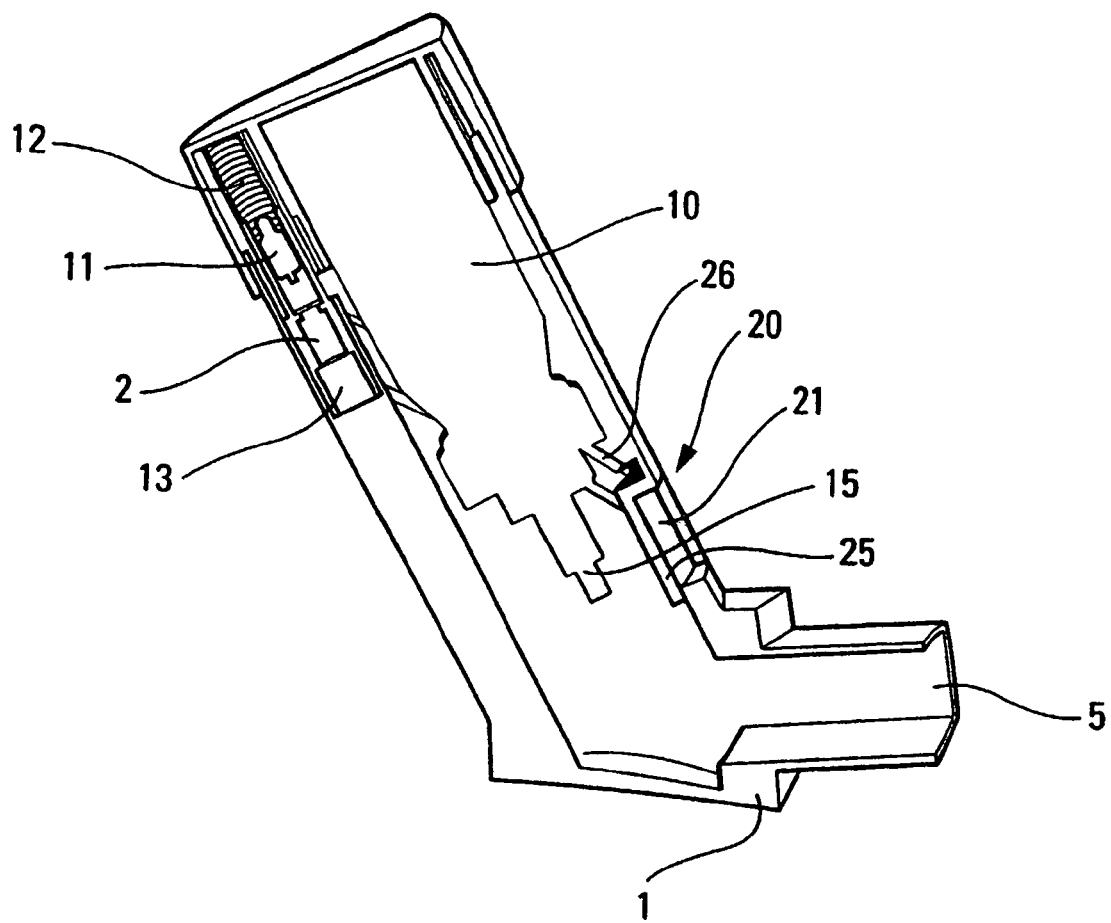
FIG. 1 is a diagrammatic side view in section of a fluid dispenser device of the present invention.

FIG. 1 shows an example of an application that is particularly adapted for the display device of the present invention. In this example, the display device 21 is used with a dose indicator or counter for a fluid dispenser. The term "fluid" refers to gases, liquids, pastes, or powders. This embodiment is particularly advantageous because the absence of an energy source, such as a battery, significantly reduces the manufacturing costs of the indicator, and makes said indicator more reliable. In the example shown the dispenser includes a body 1 in which there is mounted a reservoir 10 containing the fluid. A dispenser member 15, which, in the example shown, is a metering valve, but which could equally well be a pump, is mounted on the reservoir 10 for selectively dispensing the contents of said reservoir. The device shown in FIG. 1 is an oral inhaler including a mouthpiece 5 through which the substance is dispensed. Naturally, any other type of dispenser could be associated with the present invention. While the dispenser is being actuated, the reservoir 10 is generally displaced axially inside the body 1, thereby causing the valve 15 to be actuated. Such displacement can be used to create the electric pulse required to cause the display member 21 to change.

FIG. 1 shows an embodiment of the pulse generator, which is of the flint type. Thus, a striker pin 11 co-operating with a spring 12 is designed to come to strike a contactor 2, e.g. a piezoelectric ceramic 2 secured to an anvil 13 while the dispenser is being actuated. Advantageously, the contactor 2 is held stationary relative to the body, but naturally, any other equivalent or similar system could be used. Thus, it is possible to envisage converting friction or some other kind of impact into an electric signal. The electric signal is then transferred via power supply wires 26 to an electronic circuit 25 which co-operates with the display 21 so as to control it and change the display, and thus count each dose dispensed, corresponding to each actuation of the dispenser. As can be seen in FIG. 1, the dimensions of the dose counter are relatively small, thereby enabling the counter to be adapted in simple manner to any existing dispenser without substantially modifying its dimensions. The use of a permanent display member is particularly advantageous in that it significantly limits energy consumption, and in that it makes it possible to avoid having a battery, or any other permanent energy source, for powering the display member.

Although the display device of the present invention has been shown with reference to a particular use, it is naturally of much more general application, and it is not limited to the embodiment shown. On the contrary, any modifications could be applied thereto by a person skilled in the art, without going beyond the ambit of the present invention as defined by the accompanying claims.

The invention claimed is:

1. An electronic display device (20) including a display member (21), said device being characterized in that said display member (21) is permanent so that no energy is required to keep the display unchanged, said display device (20) operating without a battery, the energy required to change the display being created by interaction between two elements, thereby creating an electric pulse, said pulse being processed by an electronic circuit (25) before being applied to the display member (21) in order to change the display.

2. A display device according to claim 1, in which said display member (21) is of the liquid crystal display (LCD) type.

3. A display device according to claim 1, in which said display member (21) includes bistable nematic crystals.

4. A display device according to claim 1, in which said display device (20) forms part of a dose indicator or counter for a fluid dispenser device.

5. A fluid dispenser device comprising: a body (1); a fluid reservoir (10); a dispenser member (15), and a dose counter for counting the number of doses that have been dispensed or that remain to be dispensed from the reservoir (10), said device being characterized in that said dose counter includes a display device (20) according to claim 1.

6. A dispenser device according to claim 5, in which the interaction between two portions (10, 11; 1, 2) of said device moving relative to each other while the device is being actuated, is transformed by an electromechanical converter into an electric pulse used to change the display.

7. A dispenser device according to claim 5, in which the electric pulse required to change the display is created by a striker pin (11) that is displaced against a contactor (2) while the dispenser device is being actuated.

8. A dispenser device according to claim 7, in which said contactor (2) is held stationary relative to the body (1), and said striker pin (11) co-operates with a spring (12).

9. The display device according to claim 1, wherein the energy required to change the display is created by friction.

10. The display device according to claim 1, wherein the energy required to change the display is created by impact.

11. The dispenser device according to claim 5, wherein the dispenser member is a pump or a valve.

12. An electronic display device comprising a permanent display member that does not require energy to keep the display unchanged and that requires electrical energy to change the display; and
wherein the electrical energy required to change the display is generated by interaction between two physical portions of the device moving relative to each other.

13. The display according to claim 12, wherein the electrical energy required to change the display is generated without a battery.

14. The display according to claim 12, wherein the display is a liquid crystal display (LCD).

15. The display according to claim 12, wherein the display comprises bistable nematic crystals.

* * * * *